US010704059B2

United States Patent
Pardo-Lopez et al.

(10) Patent No.: US 10,704,059 B2
(45) Date of Patent: Jul. 7, 2020

(54) SUPPRESSION OF RESISTANCE IN INSECTS TO BACILLUS THURINGIENSIS CRY TOXINS THAT DO NOT REQUIRE THE CADHERIN RECEPTOR

(71) Applicants: UNIVERSIDAD NACIONAL AUTONOMA DE MEXICO, Ciudad De Mexico (MX); ARIZONA BOARD OF REGENTS ON BEHALF OF UNIVERSITY OF ARIZONA, Tucson, AZ (US)

(72) Inventors: Liliana Pardo-Lopez, Cuernavaca (MX); Bruce Elliot Tabashnik, Tucson, AZ (US); Mario Soberon-Chavez, Cuernavaca (MX); Maria Alejandra Bravo De La Parra, Cuernavaca (MX)

(73) Assignees: UNIVERSIDAD NACIONAL AUTONOMA DE MEXICO; ARIZONA BOARD OF REGENTS ON BEHALF OF UNIVERSITY OF ARIZONA

( * ) Notice: Subject to any disclaimer, the term of this patent is extended or adjusted under 35 U.S.C. 154(b) by 0 days.

(21) Appl. No.: 15/949,840

(22) Filed: Apr. 10, 2018

(65) Prior Publication Data

US 2018/0282758 A1 Oct. 4, 2018

Related U.S. Application Data

(63) Continuation of application No. 12/602,794, filed as application No. PCT/MX2007/000068 on Jun. 8, 2007, now abandoned.

(30) Foreign Application Priority Data

Jun. 8, 2007 (WO) .................. PCTMX2007000068

(51) Int. Cl.
*C12N 15/82* (2006.01)
*C07K 14/325* (2006.01)

(52) U.S. Cl.
CPC ........ *C12N 15/8286* (2013.01); *C07K 14/325* (2013.01); *Y02A 40/162* (2018.01)

(58) Field of Classification Search
CPC ........................... C12N 15/828; C07K 14/325
See application file for complete search history.

(56) References Cited

U.S. PATENT DOCUMENTS 6,114,608 A 9/2000 Mettler
2003/0167517 A1 9/2003 Arnaut et al.

OTHER PUBLICATIONS

Gomez et al (FEBS Letters 513 (2002) 242-246) (Year: 2002).*
Barton (Plant Physiol. (1987) 85, 1103-1109) (Year: 1987).*
Romeis et al (Nat Biotechnol. Jan. 2006;24(1):63-71) (Year: 2006).*
Bravo et al (Toxicon 49 (2007) 423-435)—Available online Nov. 30, 2006 (Year: 2006).*
Miranda et al (Insect Biochemistry and Molecular Biology 31 (2001) 1155-1163) (Year: 2001).*
Gomez, Isabel, et al. "Cadherin-like receptor binding facilitates proteolytic cleavage of helix α-1 in domain I and oligomer pre-pore formation of Bacillus thuringiensis Cry1Ab toxin." FEBS letters 513.2-3 (2002): 242-246. (Year: 2002).*
Boonserm, Panadda, et al.: "Crystal structure of the Mosquito-larvicidal toxin Cry4Ba and Its Biological Implications", Journal of Molecular Biology, 2005, vol. 348, pp. 363-382.
Gomez, Isabel, et al.: "Cadherin-like receptor binding facilitates proteolytic cleavage of helix a-1 in domain I and oligomer pre-pore formation of Bacillus thuringiensis Cry1Ab toxin", FEBS Letters, 2002, vol. 513, pp. 242-246.
Jimenez-Juarez, Nuria, et al.: "Bacillus thuringiensis Cry1Ab Mutants Affecting Oligomer Formation are Non-toxic to Manduca sexta Larvae", The Journal of Biological Chemistry, 2007, vol. 282, pp. 21222-21229.
Konecka, Edyta, et al.: "Insecticidal Activity of Bacillus thuringiensis Strains Isolated from Soil and Water", The Scientific World Journal, 2012, Article ID 710501.
Miranda, Raul, et al.: "Processing of Cry1Ab d-endotoxin from Bacillus thuringeiensis by Manduca sexta and Spodoptera frugiperda midgut proteases: role in protoxin activiation and toxin inactivation", Insect Biochem. Molecular Biology, 2001, vol. 31, pp. 1155-1163.
Soberon, Mario, et al.: "Engineering Modified Bt Toxins to Counter Insect Resistance", Science, 2007, vol. 318, pp. 1640-1642.
International Search Report, PCT/MX2007/000068.

* cited by examiner

*Primary Examiner* — Lee A Visone

(57) ABSTRACT

The present invention provides a method to obtain DNA constructs that encode 3-domain Cry toxins (also called Cry toxins, Bt toxins, or β-endotoxins) lacking helix α-1. These DNA constructs have been modified to encode proteins that kill insects that are resistant to the corresponding unmodified Cry toxins. The DNA constructs encoding the Modified 3-Domain Cry Toxins and the encoded Modified 3-Domain Cry Toxins are provided together with the molecular vectors and the host cell comprising said constructs and the recombinant methods to produce the Modified 3-Domain Cry Toxins. Additionally, compositions comprising the Modified 3-Domain Cry Toxins are disclosed. The resistance of the insects to unmodified Cry toxins is due to reduced toxin binding to the insects' midgut receptors. The invention further provides methods to overcome resistance in crop pests.

6 Claims, 6 Drawing Sheets

Figure 1:
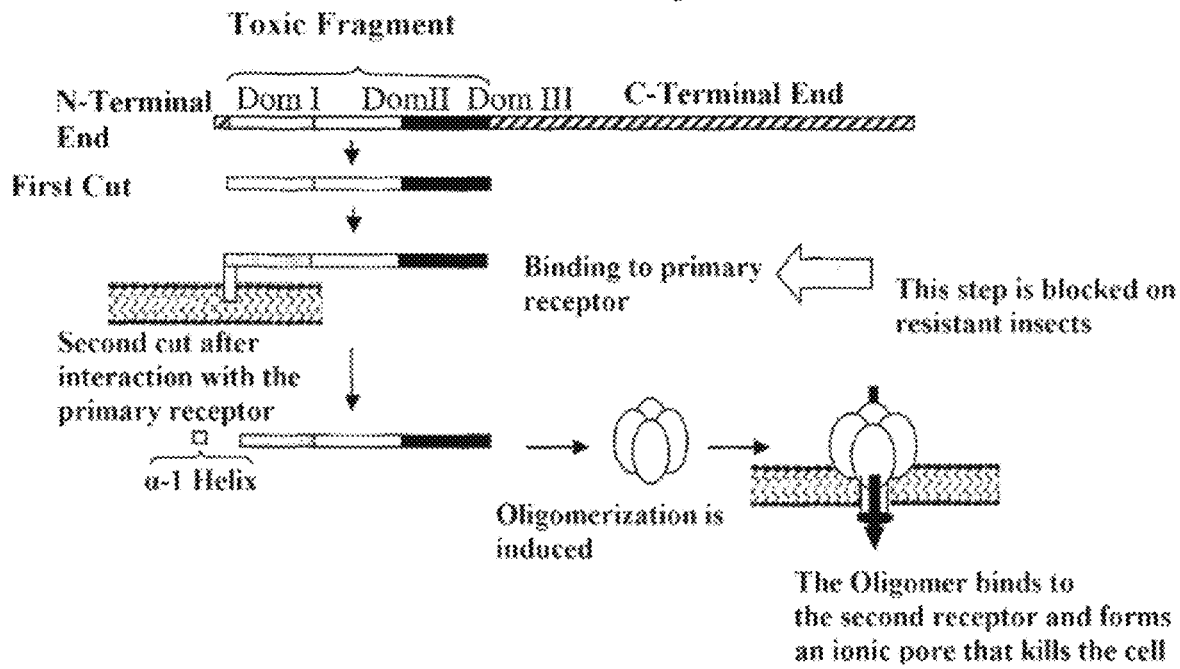

Specification includes a Sequence Listing.

▨ Region of the promoter (390 bp)

▨ Amino terminal end containing the α-1 helix

▨ Region of the toxin from the α-2 helix to β-23 (1687 bp)

☐ Fragment of the C-terminal end of the protoxin (2069 bp)

▨ Region of the terminator (368 bp)

A = Cry1Ac-mod
B = Cry1Ab-mod
C = Cry1Ab

A = CADR11-12
B = CADR 7-11
C = CADR 7-12
D = CADR12

E = scFv73 (1:4)
F = scFv73 (1:1)
G = control

A = Cry1Ab-mod
B = Cry1Ac-mod
C

A = Markers
B = Bt-R1
C = 28 i Mal

SUPPRESSION OF RESISTANCE IN INSECTS TO BACILLUS THURINGIENSIS CRY TOXINS THAT DO NOT REQUIRE THE CADHERIN RECEPTOR

Cry toxins of *Bacillus thuringiensis* (Bt) are valuable for their ability to control insect pests in different cultivars, forests, and insects that transmit disease in humans. The development of resistance in insect infestations to the Bt toxins is the principal obstacle for continuing success in the use of this insecticide, which is environmentally friendly. The main mechanism in insects of resistance to the Cry toxins involves a reduction in binding of the Cry toxins to the specific receptors located in the insects' gut. (Ferré and Van Rie, 2002).

The Cry1A proteins are a group of Bt toxins that kill some key lepidopterous insects. In strains of the three principal cotton pests [*Heliothis virescens* (Gahan et al, 2001), *Pectinophora gossypiella* (Morin et al, 2003) and *Helicoverpa armigera* (Xu et al., 2005)], resistance to the Cry1A toxins is linked to changes in the cadherin protein, which acts as the primary receptor for Cry toxins in the intestine of vulnerable insects. Mutations in the cadherin gene produce "Type 1" resistance to the Bt toxins, this type of resistance is the resistance that presents with the greatest frequency in different insects. This type of resistance, which presents high levels of resistance to at least one Cry1A toxin, is of a recessive nature, reduces the binding of at least one Cry1A toxin to the resistant insect's membranes and presents very little cross resistance to the toxin Cry1C (Ferré and Van Rie, 2002). Interestingly, the diamondback worm (DBM), *Plutella xylostella*, a world-wide pest that attacks vegetables such as broccoli and cauliflower, presents "type 1" resistance to the Cry1A toxins but in this case it is not directly associated with mutations in the *cadherin* gene. The DBM is the only Bt toxin resistant insect in the entire world that was selected in the field (Tabashnik, 2004). Binding to cadherin facilitates the proteolytic cut of the α-1 helix of Domain I and the formation of a oligomeric pre-pore which is responsible for the toxicity of these proteins (Gomez et al, 2002).

In this invention, it is demonstrated that Modified 3-Domains Cry Toxins produced from 3-Domain Cry gene constructions lacking the DNA for encoding Helix α-1, kills insects that are resistant to the wild 3-Domain Cry toxins (Unmodified Cry Toxins).

The genetic basis of the resistance of insects to Unmodified 3-Domain Cry Toxins is linked to mutations in the cadherin gene that encodes the primary receptor of the Cry1A toxins. In resistant insects, the primary receptor is truncated or absent, so the binding of Cry toxins to the membranes of the intestinal cells is reduced or absent. Therefore, resistant insects are not sensitive to Unmodified 3-Domain Cry Toxins The Modified 3-Domain Cry Toxins that are presented in this invention suppress resistance by not requiring binding of the toxin to the cadherin receptor. The toxicity of the Modified 3-Domain Cry Toxins was demonstrated against two strains of insects resistant to wild Cry1A toxins and was also tested on insects with a reduced vulnerability to Cry toxins induced by silencing the cadherin RNA. One strain of resistant insects presents Type 1 resistance by genetic modification of the cadherin gene, while the other strain presents Type 1 resistance not linked to mutations in the cadherin gene.

Modified Cry1A proteins produced by building genes lacking the α-1 helix induced the in vitro formation of the oligomeric pre-pore without requiring binding to the cadherin receptor, nor fragments of the cadherin protein containing the Cry toxin binding sites or the antibody in the scFv (scFv73) format, which mimetizes the Cry toxin binding region present in the cadherin receptor (Gomez et al., 2002). On the other hand, Unmodified Cry1A proteins require the presence of the scFv73 antibody or fragments of the cadherin protein or cadherin to produce the oligomeric pre-pore in vitro.

The invention herein described could have very broad applications due to the similarity that exists in the Cry1A proteins' mode of action with other 3-Domain Cry Toxins, as well as the presence of various insects having a common resistance mechanism to the Cry toxins. In addition to the Cry1A proteins, there are many other Bt toxins that are Cry toxins having a 3-Domain structure, in which proteins with low similitude in the amino acid sequence are included (de Maagd et al. 2001). It has been reported that different 3-Domain Cry Toxins (Cry1A, Cry1B, Cry1C, Cry1D, Cry1E, Cry1F, Cry3A, Cry3B, Cry3C, Cry4A, Cry4B y Cry11) form oligomeric structures similar to those observed with the Cry1Ab toxin and that are inserted into the membrane of target larval intestinal cells, forming ionic pores. This suggest that the 3-Domain Cry proteins have a mechanism with an similar action (Gomez et al, 2002; Rausell et al, 2004a, Rausell et al, 2004b; Herrero, S. et al, 2004; Muñoz-Garay et al, 2006). Moreover, the most common resistance mechanism in insects to the Cry1A toxins involves alterations in the primary cadherin receptor. These alterations avoid the formation of oligomeric pre-pore structures that normally are mediated by the interaction of the Cry toxin with the cadherin receptor. Therefore, we predict that different insects resistant to Unmodified 3-Domain Cry Toxins may be sensitive to the corresponding Modified 3-Domain Cry Toxins, from which the fragment that encodes the α-1 helix was revealed. The Modified 3-Domain Cry Toxins produced by the genetic constructions here described may be presented to the insect population as topically applied insecticides (for example, as a spray insecticide), as transgenic microorganisms, or as transgenic plants.

BACKGROUND

*Bacillus thuringiensis* (Bt) is a bacteria belonging to the *Bacillus cereus* group (Helgason et al 2000). Unlike other members of the *Bacillus cereus* group, Bt produces parasporal crystals that are principally made up of insecticide proteins called Cry toxins, Bt toxins, or δ-endotoxins.

Bt toxins are toxic for some specific insects and are non-toxic to humans, vertebrates, and plants. They are also completely biodegradable. Therefore, Bt toxins are safe and effective in controlling pest insects. The applications for these toxins include: 1) controlling defoliating infestations in forests, 2) controlling mosquitoes and black flies which are vectors for disease in humans, 3) controlling agricultural infestations by using insecticide formulations containing Bt toxins or microorganisms that express them, and 4) controlling agricultural infestations by us ing transgenic plants that produce Bt toxins.

Cry proteins may divide into several groups according to their homology. The group that contains the greatest number of Cry toxin variants is the 3-Domain Cry protein group. Other groups of Cry toxin homology include Cry toxins similar to Bin and Mtx toxins produced by *Bacillus sphaericus* (Crickmore et al, 1998; Crickmore et al, 2002).

To date a large quantity of Bt strains have been isolated, finding toxins active to lepidopteran, dipteran, or coleopteran insects (Schnepf et al. 1998). The Cry toxins kill insects because they form lytic pores in the membrane of the epithelial cells of the intestine of the larva.

Structure of the 3-Domain Cry Toxins.

The members of the 3-Domain Cry Toxins family are globular proteins shaped by three domains linked via simple linkers. The three dimensional structures of the toxins active with Cry1Aa proteases (specific to Lepidoptera), Cry3A, Cry3B (specific to Coleoptera), Cry4Aa and Cry4Ba (specific to Diptera) and Cry2Aa protoxin (specific to Diptera and Lepidoptera) have been reported (Grouchulski et al, 1995; Li et al, 1991; Galistki et al, 2001; Morse et al, 2001; Boomserm et al, 2005; Boomserm et al, 2006). The sequence identity is low among some of these toxins. For example, between the Cry2Aa and Cry3Aa there is 20% identity and the toxins Cry2Aa and Cry1Aa present only 17% identity of its sequences. In spite of the low sequence identity of these toxins, their three dimensional structure is similar, suggesting that they share similar action mechanisms (FIG. 1).

Each toxin of the 3-Domain Cry toxin family has three structural domains, called I, II, and III. Domain I is formed by branching of seven α-helixes in which the central helix (α5 helix) is surrounded by the external helixes. The α5 helix is highly conserved within the 3-Domain Cry toxin family. This domain has been involved in the formation of the ionic pore in the target insect membrane. Domain II consists of three antiparallel β-sheets packed around a hydrophobic center which forms a β-structure prism. Domain II has been designated as the domain determining specificity, it is the most variable domain (de Maagd et al, 2001). The amino acid residues involved in the contacts between domains I and II (present in the α-7 helix and the β-1 sheet) are highly conserved in the Cry family of toxins. Domain III is formed by two antiparallel β-sheets. This domain is also involved in specificity and interaction with the receptor (de Maagd et al, 2001). The contacts between domain II and III (that corresponds to β-11 and β-12 sheets) as well as the interior area of domain III (that corresponds to β-17 and β-23 sheets) also are highly conserved within the 3-Domain Cry toxin family.

Mechanism of Action

In order to kill insects, the 3-Domain Cry toxins are converted from parasporal crystals made up of protoxins to ionic channels formed by oligomeric structures inserted in the membrane that causes an output of ions and cellular lysis. The parasporal crystal is ingested by the vulnerable larva; this crystal is solubilized within the intestine of the larva. As shown in FIG. 1, the solubilized protoxins are cut by the proteases of the intestine producing proteic fragments of 60-70 kDa (de Maagd et al, 2001). This initial activation of the toxin involves proteolytic processing of the N-terminal end (25-30 amino acids for Cry1 toxins, 58 residues for Cry3 toxins and 49 for Cry2Aa) and in the case of the long Cry protoxins of 130 kDa (Cry1, Cry4, Cry5, Cry7-Cry14, Cry16-21, Cry24-Cry32, Cry39-44, Cry47-48 and Cry50) approximately half the protein is also processed in its C-terminal end.

After the initial proteolytic cut, the toxin binds to specific receptors in the apical membrane microvilli (brush border) of the columnar cells present in the intestinal epithelium (Schnepf et al, 1998; de Maagd et al, 2001). The interaction with the primary receptor induces a second proteolytic cut of the toxin where the α-1 helix is removed. After the second cut, the toxin molecule is completely activated and may associate with other similar molecules to form an oligomeric structure. The oligomer of the toxin presents a high affinity for the second receptor (aminopeptidase or alkaline phosphatase). The interaction with the second receptor facilitates the insertion in the microdomains of the membrane (Schnepf et al, 1998; Aronson y Shai, 2001; Bravo et al 2004; Pardo et al 2006). The insertion of the toxin leads to the formation of lytic pores in the apical membrane microvilli, and finally to the death of the cells (Schnepf et al, 1998; Aronson y Shai, 2001).

At least four different proteins in lepidopterous insects have been described that are capable of binding to Cry1A toxins: The primary receptor is characterized as a protein similar to the cadherins (CADR); the secondary receptors are two proteins anchored to the membrane by a bridge of glycosylphosphatidyl inositol (GPI), aminopeptidase-N (APN) and alkaline phosphatase (FAL). Finally, a glycoconjugate of 270 kDa has also been reported as a possible primary receptor (Vadlamudi et al, 1995; Knight et al, 1994; Jurat-Fuentes et al, 2004; Valaitis et al, 2001).

In this invention we will use the abbreviation CADR to refer to the cadherin type of proteins that act as primary receptor for one or more Bt toxins. Due to the fact that a systematic nomenclature for these proteins has not yet been established, the names of the different CADRs present in different insects vary, for example, Bt-$R_1$ for the cadherin of *Manduca sexta* (Vadlamudi et al, 1995) and BtR for *P. gossypiella* (Morin et al, 2003). The CADRs are transmembrane proteins with a cytoplasmic domain and with an extracellular ectodomain that contains various repeated motifs that characterize the cadherins, 12 repeated motifs in the case of Bt-$R_1$ (Vadlamudi et al, 1995). These ectodomains contain calcium binding sites, interaction sequences with integrins and cadherin binding sequences.

The sequential process in the interaction of the toxin with different receptors has been described in detail for the Cry1A toxin in *Manduca sexta*. In this insect, the toxin first binds to the primary Bt-$R_1$ receptor. After the toxin oligomerizes, it binds to the secondary receptors anchored by GPI to the membrane, APN or FAL (Bravo et al, 2004; Jurat-Fuentes et al, 2006).

Binding of the Cry1Ab to the Bt-$R_1$ in *M. sexta* promotes an additional proteolytic cut in the N-terminal end of the toxin (removing the α-1 helix). This cut facilitates the formation of a pre-pore with an oligomeric structure that increases its affinity to the secondary receptor and that is important for the insertion of the toxin into the membrane and for toxicity (Gomez et al, 2002; Rausell et al, 2004a). Incubation of the Cry1Ab protoxin with proteases present in the *M. sexta* gut in the presence of the simple chain antibody scFv73, which mimetizes to the binding site present on the Bt-$R_1$ receptor, also produces toxin preparations containing the oligomer of 250 kDa, which lacks the domain I α-1 helix (Gomez et al, 2002, 2003). This oligomer of 250 kDa also forms when the Cry1Ab protoxin is incubated with the proteases of the *M. sexta* gut in the presence of peptides that contain the Bt-$R_1$ receptor sequence for the specific bond of the toxin (repeated regions on CADR 7 and 11) (Gomez et al, 2002, 2003).

The oligomeric structures of Cry1Ab and Cry1Ac increase their affinity to bind to the secondary APN receptor some 100 to 200 times, showing constants of apparent disassociations of 0.75-1 nM (Gomez et al, 2003, Pardo et al, 2006). The oligomer of 250 kDa, in contrast to the monomer of 60 kDa, is membrane insertion competent (Rausell et al, 2004a). Analysis of pore formation in flat lipid bilayers constructed with synthetic lipids demonstrated the differences in Cry1Ab oligomer and monomer pore formation. First, pore formation occurs at a much lower concentration with the oligomer than with the monomer. Second, the ionic channels induced by the oligomer are more stable and present a high probability of opening unlike those induced by monomers (Rausell et al, 2004a).

The formation of oligomers from Cry toxins has been demonstrated for the Cry1Aa, Cry1Ab, Cry1Ca, Cry1 Da, Cry1 Ea, Cry1 Fa, Cry1Ca, Cry3A, Cry3B, Cry3C and Cry4B toxins (Gomez et al, 2002; Rausell et al, 2004a, Rausell et al, 2004b; Herrero, S. et al, 2004; Munoz-Garay et al, 2006; Tigue, et al. 2001; Likitvivatanavong, et al. 2006). The Cry11Aa toxin also oligomerize in the presence of their receptors (Perez, personal communication). In all of these cases, pore formation activity was much greater in the toxin samples that contained oligomeric structures in contrast to those that only contained monomeric structures of the toxin. This data supports the hypothesis that the formation of Cry toxin oligomers increases the toxicity of these proteins. APN and FAL receptors have been implicated in the process of inserting the Cry1A toxins into the membrane. Removal of APN and FAL via a GPI cut with a phospholipase C treatment specific for phosphatidyl inositol (this enzyme removes the GPI-anchored proteins) significantly abate the Cry1Ab oligomer levels inserted into membrane microdomains and drastically reduce toxin pore formation activity (Bravo et al, 2004). Furthermore, incorporating APN in synthetic flat bilayers increases the Cry1Aa pore forming activity (Schwartz et al, 1997).

Based on the data described above, a model of the action mechanism of the Cry1A toxins is proposed, which involves the sequential interaction of the Cry1A toxins first with the Bt-$R_1$ receptor and then with the APN-FAL molecules. The interaction of the Cry1A monomer with the cadherin receptor facilitates the formation of a oligomeric pre-pore structure which presents an increase in the affinity of the bond with the second APN or FAL receptor. The pre-pore of the toxin then binds with APN or FAL. Finally, the pre-pore of the toxin is inserted in the membrane microdomains (or lipid rafts) inducing pore formation and cellular lysis (Bravo et al, 2004).

Resistance in Insects to the Cry Toxins.

The main resistance mechanism to the Cry toxins involves a reduction in binding of the toxin to the receptors located in the insects' gut (Ferré and Van Rie, 2002). Mutation sin genes that encode CADRs are strongly linked to resistance to Cry1A toxins in at least three extremely important insect pests: *H. virescens* (Gahan et al, 2001), *Pectinophora gossypiella* (pink bollworm) (Morin et al, 2003) and *Helicoverpa armigera* (Xu et al, 2005). In the case of the diamondback worm (DBM), *Plutella xylostella*, a world-wide pest that attacks vegetables such as broccoli and cauliflower, the "type 1" resistance is not directly linked to mutations in the cadherin gene. Nevertheless, it is possible that the mutation in this line of resistant insects may indirectly affect the expression of the cadherin protein (Baxter et al 2005).t The creation of transgenic crops that produce Cry toxins to kill the principal pest insects is a defining moment in the reduction of chemical insecticide use and an increase in the use of alternatives that are environmentally compatible and friendly for the control of insects. Cry toxins are continuously produced in transgenic plants, which allows them to control insect borers that are protected from surface sprayed chemical insecticides. The production of Cry toxins has been improved through genetic engineering of the Cry genes to have a codon use that is compatible to that of the plants, eliminating possible RNA processing sequences and cutting the protoxin C-terminal region (Schuler et al, 1998).

Insect resistant transgenic plants have been used on a large scale since 1996. Bt-corn and Bt-cotton have been grown on 26 million hectares (James 2005). This very broad use of Bt crops incites an intense selective pressure for Bt toxin resistance in insect pest populations (Tabashnik 1994, Gould 1998). If the insect pest develops resistance, the usefulness of the Bt toxins ends. In response to this challenge, strategies to manage resistance have been developed and implemented to prolong the effectiveness of the Bt crops.

The principal strategy to prevent resistance in Bt crops is the use of refuges (Gould 1998). Refuges are areas of non-transgenic crops grown near Bt crops. The objective of the refuge strategy is to retrace the resistance maintaining populations of vulnerable insects that may mate with resistant insects. In the majority of the cases studied, the resistance to Cry toxins is conferred through recessive mutations (Ferré y Van Rie, 2002; Conner et al, 2003; Tabashnik et al, 2003). With recessive resistance, crossbreeding between resistant homozygote insects that may emerge from Bt crops with vulnerable homozygote insects of the refuge area will produce heterozygote offspring that is vulnerable to the Cry toxin expressed by the Bt crops. Although this strategy seems to be useful to retrace the resistance, meticulous large scale field trials have not been performed (Tabashnik et al, 2005). In any case, the refuge strategy assumes resistance will be retraced, not prevented.

Resistance to Bt crops in the field has not yet been reported, nevertheless laboratory selection has generated Bt resistant strains in many insect pests. (Tabashnik, 1994; Ferré and Van Rie, 2002; Tabashnik, et al, 2003). Additionally, resistance to the spray Bt toxins has developed in the field in the diamondback worm, *Plutella xylostella* (L.), and in greenhouse populations of cauliflower 100 pers, *Trichoplusia ni* (Hübner) (Tabashnik, 1994; Ferré y Van Rie, 2002; Janmaat and Meyers, 2003; Tabashnik et al, 2003). With extensive use of Bt toxins throughout the world and with the rapid increase in its use, resistance in insect pests to the Cry toxins currently used, is an increasingly significant threat to human health, food production, and the environment. Therefore, modified cry toxins that kill resistant insects are desirable and absolutely necessary.

DETAILED DESCRIPTION OF THE FIGURES

FIG. 1—Mechanism of Action of the Unmodified 3-Domain Cry Toxins.

Figure 2:
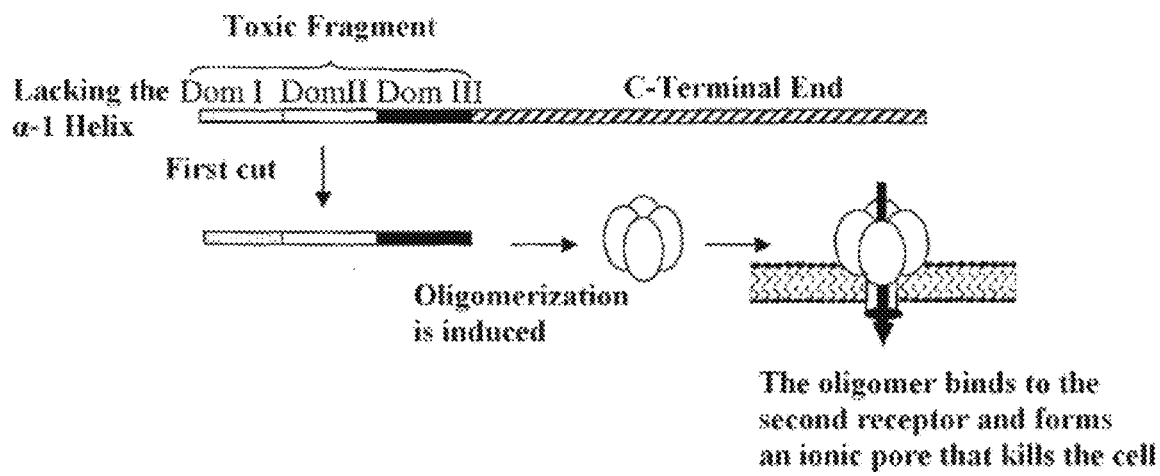

FIG. 2—Mechanism of Action of the Modified 3-Domain Cry Toxins.

Figure 3:
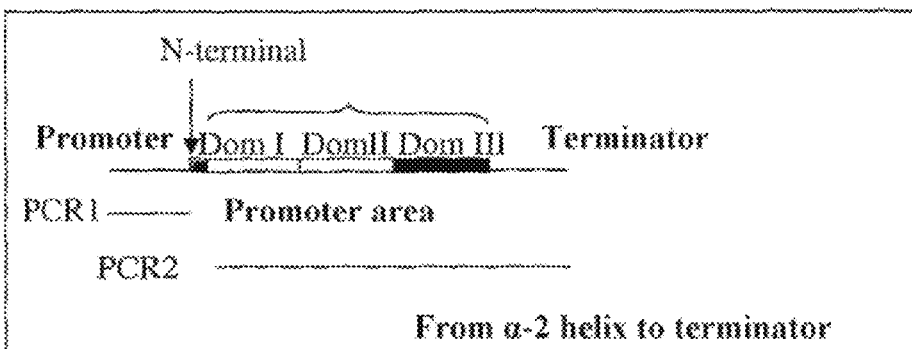
Figure 3:
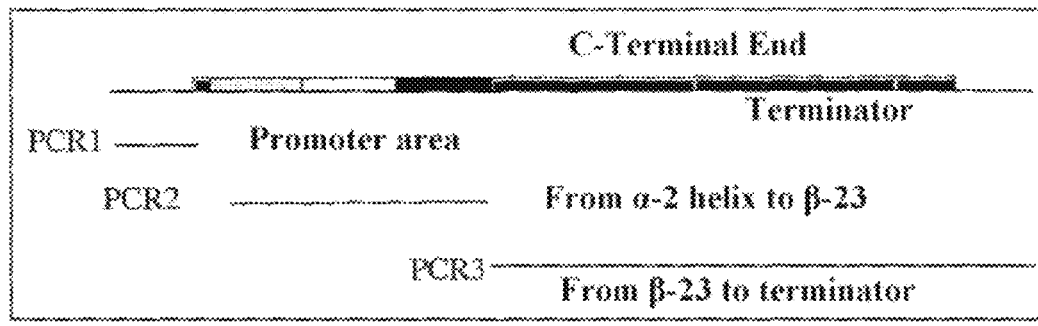
Figure 4:
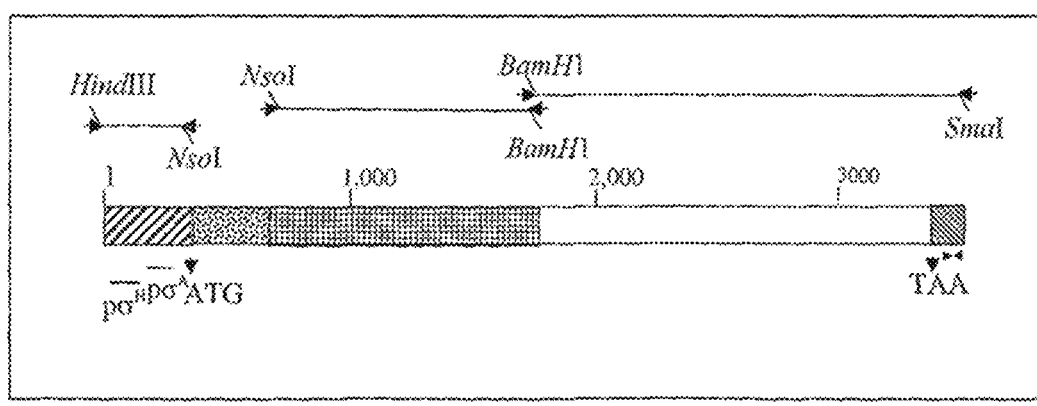

FIG. 3—Design of firsts [SIC] for PCR reaction of the long (130 kDa) and short (70 kDa) Cry toxins FIG. 4—PCR strategy for the production of Cry1Ab and Cry1Ac lacking the N-terminal end of the protein up to the end of the α-1 helix.

Figure 5:
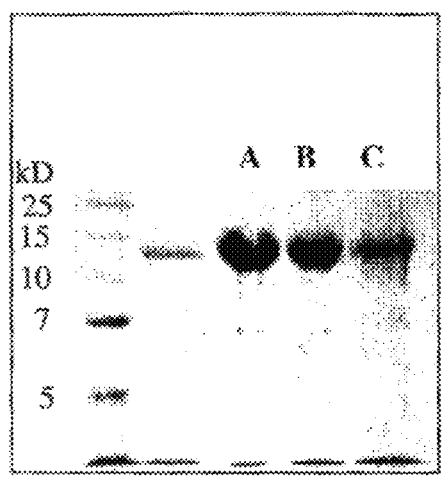

FIG. 5—SDS-PAGE acrylamide gel electrophoresis of mutant Modified Cry1Ab and Cry1Ac Toxins without the α-1 helix demonstrating the production of a 130 kDa protoxin protein.

Figure 6:
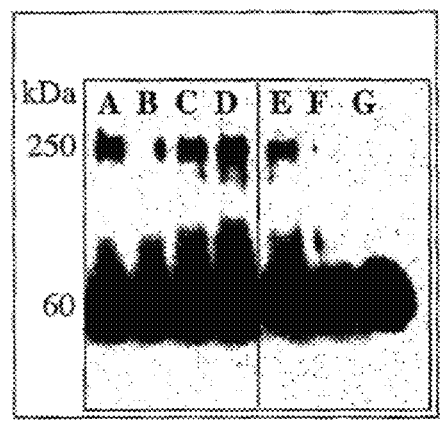

FIG. 6—Detection via Western Blotting immunodetection of the oligomeric structure (250 kDa) of the unmodified Cry1Ab toxin obtained after incubating the Cry1Ab protoxin with gastric juice from the gut of the *Manduca sexta* in the presence of CADR proteic fragments (containing repetitions 7-12, 11-12 or 12) or in the presence of the scFv73 antibody or with no CADR fragment or antibody (control).

Figure 7:
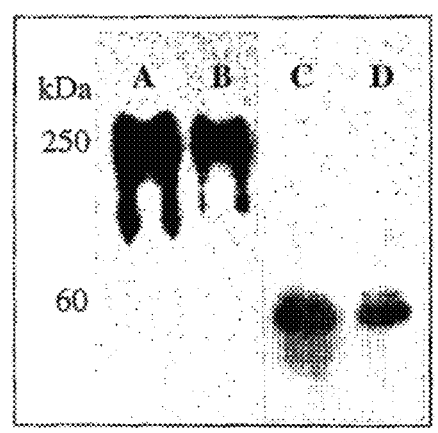

FIG. 7—Detection of the oligomeric structures (250 kDa) via Western Blotting immunodetection obtained only by treating the Modified 3-Domain Cry Toxins, Cry1AbMod and Cry1AcMod with trypsin.

Figure 8:
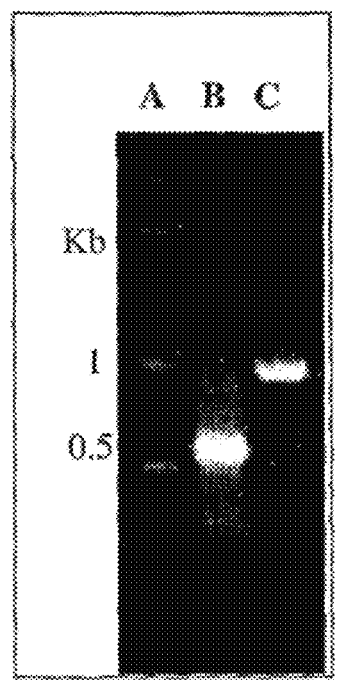

FIG. 8—Agarose gel electrophoresis showing the double chain RNA (dsRNA) of the Bt-$R_1$ gene fragment and gene control obtained after the in vitro transcription with T7 polymerase.

Figure 9:
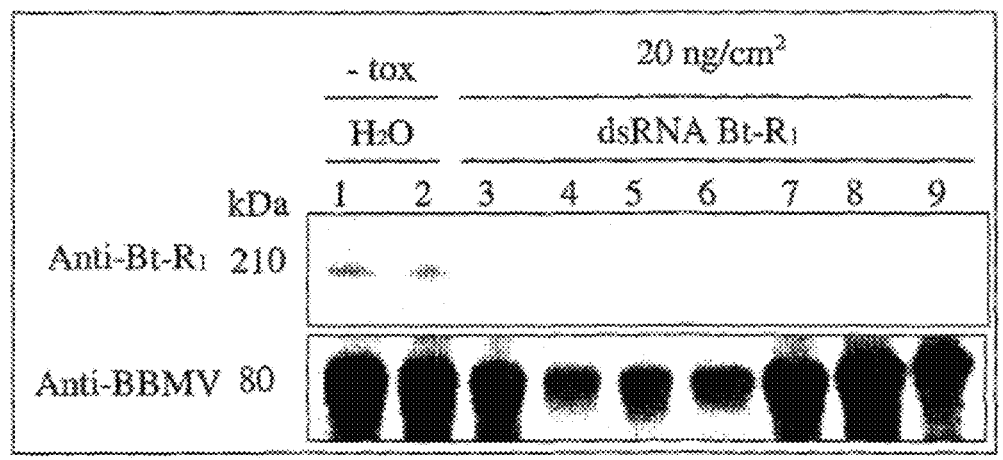

FIG. 9—Detection of the larval gut homogenates (10 μg) via Western Blotting immunodetection revealed with the anti Bt-R1 antibody or with the antibody against the total proteins of the apical membrane microvilli of the gut (anti-BBMV). The controls (lines 1 and 2) are two separate larvae that were injected with water and cultivated on an artificial diet without toxin. Samples of the gut of 7 separate larvae (lines 3 to 9) that were injected with 1 μg dsRNA Bt-$R_1$ and cultivated on an artificial diet with 20 ng Cry1 Ab/$cm^2$.

Figure 10:
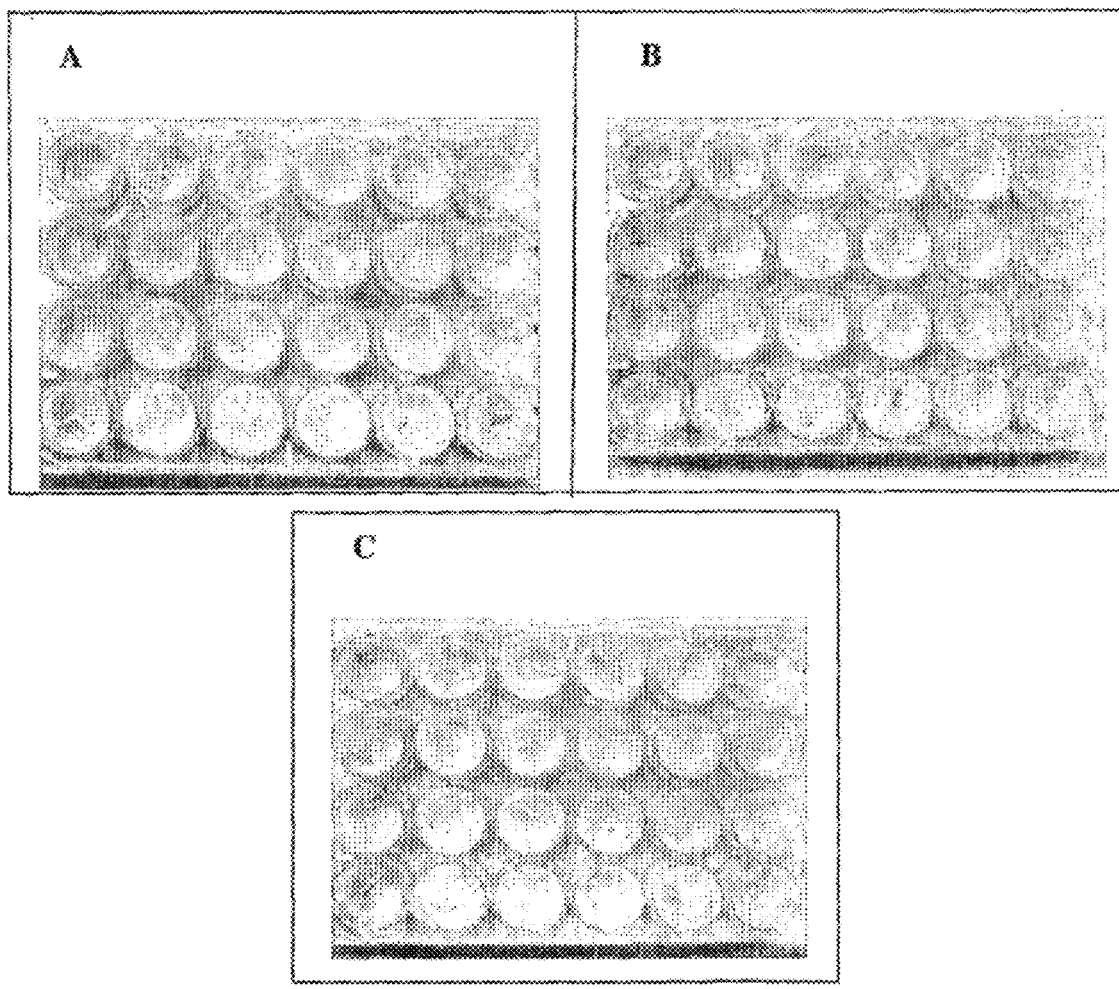

FIG. 10—*Manduca sexta* larvae injected with 1 μg of Bt-$R_1$ dsRNA and incubated in Petri boxes for three days on an artificial diet with: A) 20 ng Cry1Ab/$cm^2$; B) 5 ng Cry1AbMod/$cm^2$; C) water (control).

DETAILED DESCRIPTION OF THE INVENTION

Definitions.

The term "3-Domain Cry Toxin(s)" refers to one (a few) member(s) of a subgroup of the insecticidal crystal protein family also called Cry toxins, Bt toxins, or δ-endotoxinas, that are globular proteins made up by three different structural domains (I, II and III) linked by simple bonds. Although the sequence identity among some of these toxins is low, their structural topology is similar, suggesting that they share a similar action mechanism (FIG. 1). Among these 3-domain toxins, this invention targets a very well known group of short Cry toxins in particular (Cry3, Cry2 and Cry11) and long cry toxins (Cry1, Cry4, Cry5, Cry7, Cry8, Cry9, Cry10, Cry11, Cry12, Cry13, Cry 14, Cry 16, Cry17, Cry18, Cry19, Cry20, Cry21, Cry24, Cry25, Cry26, Cry27, Cry28, Cry29, Cry30, Cry31, Cry32, Cry39, Cry40, Cry41, Cry42, Cry43, Cry44, Cry47, Cry48 and Cry50), which share a mechanism of action. To kill the insects, these toxins must bind to a primary receptor before forming an oligomeric structure that inserts itself into the membrane to create pores.

The term "Unmodified 3-Domain Cry Toxin(s)" stands for the wild 3-Domain Cry Toxin that has not been modified. These unmodified toxins requires binding to the first receptor and must be enzymatic processed, removing the α-1 helix in order to be completely activated and toxic to vulnerable larva (FIG. 1).

The term "Modified 3-Domain Cry Toxin(s)" stands for the 3-Domain Cry Toxins that were modified so that they lack the α-1 helix. These toxins do not require binding to the first receptor nor do they require their α-1 helix be enzymatically processed to become active (FIG. 2).

The terms "Cry1AbMod" and "Cry1AcMod" stands for the two individual Modified 3-Domain Cry Toxins that lack the α-1 helix, and that correspond to Unmodified 3-Domain Cry Toxins, Cry1Ab and Cry1Ac, respectively.

The term "Eligible Resistant Insects" refers to the insects resistant to Unmodified 3-Domain Cry Toxins whose resistance is linked to mutations that affect the expression of the primary receptor gene (called cadherin for Cry1A toxins), whether the mutations are directly present in the primary receptor gene or in other genes that affect the expression of said primary receptor.

Since when the primary receptor is modified, truncated, or not expressed, the bond of the Unmodified 3-Domain Cry Toxins to the apical membrane of the gut cells is reduced or eliminated and the toxin cannot be completely activated, the oligomer is not formed, it does not insert itself into the membrane and it does not kill the insects. Therefore, these insects are resistant to the Unmodified 3-Domain Cry Toxins. These resistant insects are the target of the Modified 3-Domain Cry Toxins of this invention where the Modified 3-Domain Cry Toxins suppress the resistance of the insects that are already capable of forming the oligomer, of inserting themselves into the membrane and finally, of killing these resistant insects.

As was said above, there is a problem that may presently be an issue of major importance in agriculture, forests, and public health. This problem is the appearance of resistance to the Unmodified 3-Domain Cry Toxins in insect pests that are continually exposed to these toxins, since these toxins are sprayed or produced by transgenic plants. Different strategies have emerged to retrace this problem, but it is not expected that these strategies will prevent or resolve it once it occurs.

The inventors of this invention designed and put into practice a way to suppress resistance to the Unmodified 3-Domain Cry Toxins in insects by the Eligible Resistant Insects with the Modified 3-Domain Cry Toxins which bypass two steps in the mechanism of action of the Unmodified 3-Domain Cry Toxins (FIG. 2): 1) the bond between the toxin and the primary receptor and 2) the additional proteolytic cut in the N-terminal end of the toxin that makes cutting the α-1 helix possible. These steps are required to facilitate the formation of a pre-pore with an oligomeric structure for the Unmodified 3-Domain Cry Toxins, the oligomeric pre-pore is important for the insertion of the toxin into the membrane and for toxicity (Gomez et al, 2002; Rausell et al, 2004a).

This invention is based on knowledge of the mechanism of action of certain members of the 3-Domain Cry family (illustrated in FIG. 1), which it is hoped will be common for the other members of the 3-Domain Cry toxin family (Bravo et al., 2004; Gomez et al, 2002; Rausell et al, 2004a, Rausell et al, 2004b; Herrero, S. et al, 2004; Muñoz-Garay et al, 2006). This invention is also based on the knowledge that defects in the primary receptor constitute the most common and important mechanism by which insects become resistant to the Cry toxins (Ganan et al, 2001, Ferre and Van Rie, 2002; Morin et al, 2003; Xu et al, 2005).

In the first scope, this invention relates to a method for obtaining DNA constructions coding for 3-domain Cry toxins which lack the α-1 helix. As has been mentioned above, the in vitro enzymatic cut of this portion of the toxin facilitates the formation of an oligomeric pre-pore in the Unmodified 3-Domain Cry Toxins (FIG. 1). In contrast to the Unmodified 3-Domain Cry Toxins, neither the toxicity of or the binding to the primary receptor (CADR for Cry1A toxins) or the enzymatic cut of the α-1 helix of the referenced Modified 3-Domain Cry Toxins require association with the bond to the primary receptor (FIG. 2). These DNA constructions are useful for producing Modified 3-Domain Cry Toxins that bypass the binding step with the primary receptor and the enzymatic cut of the α-1 helix. The Modified 3-Domain Cry Toxins are useful whether they are produced by transgenic plants or expressed in other systems as microorganisms or applied in another way such as spray insecticides.

The method to obtain DNA constructions coding for Modified 3-domain Cry toxins lacking the α-1 helix consists of the following steps:

a) Select the target gene of the 3-Domain Cry toxin that you wish to modify.

b) Identify the area of the promoter, the area that encodes the protein fragment and the coding area for the α-1 helix.

c) Amplify the gene excluding the area that encodes the amino-terminal end and the α-1 helix.

Amplification of the gene lacking the α-1 helix may be performed using the chain reaction of the polymerase (PCR), using a proper DNA template containing the Unmodified 3-Domain Cry toxin gene that has been selected. This is done in two or more amplification steps, depending on the size of the gene and on the fragments that you wish to use. The first step of amplification (PCR1) amplifies only the promoter area, the second PCR (PCR2) and the subsequent amplification steps (PCR3) amplify the coding area beginning at the α-2 helix going up to the β-23 and also amplify (if it is present) the area corresponding to the carboxyl-terminus end of the protein.

For the PCR1, oligonucleotides are designed first from the amplification reaction that includes the start codon (ATG) and the internal restriction site Ncol. For PCR2 and the following amplifications, the oligonucleotides must be designed to obtain the number of DNA fragments desired to include the coding area of the protein including from the α-2 helix up to the β-23 sheet. The carboxyl-terminus end of the protein, if it is present in the selected 3-Domain Cry Toxin, must also be amplified including the terminator area of the protein.

Preferably, the oligonucleotides must include restriction sites in their 5' ends that are not present in the selected gene. The internal Ncol site may be used to bind the product of the PCR1 with that of the PCR2. The restriction sites will be selected in such a way that the 3' end of the product of the PCR-1 reaction may be linked only at the 5' end of the product of the PCR-2 reaction, and the 3' ends of the product of the PCR-2 may be linked only at the 5' end of the product of the PCR-3 and so forth. (FIG. 3). Preferably, the specific restriction sites that are included in the 5' end of the product of the PCR1 containing the promoter area and in the 3' end of the PCR that contains the terminator must be used to bind these DNA fragments to a proper plasmid vector.

The application of this method is illustrated in Example 1 for the Cry1A and Cry1Ac toxins. However, this may be applied for any other Unmodified 3-Domain Cry Toxin to obtain the corresponding Modified 3-Domain Cry Toxin lacking the α-1 helix. The web page of Neil Crickmore (Crickmore, N., Zeigler, D. R., Schnepf, E., Van Rie, J., Lereclus, D., Baum, J, Bravo, A. and Dean, D. H. *"Bacillus thuringiensis* toxina nomenclature" 2005, at the website lifesci.sussex.ac.uk/Home/Neil Criekmore/Bt/, which can be accessed using the http prefix) lists the majority of the known Cry toxins and the 3-Domain Cry toxins, including the NCBI access numbers of their coding DNA. Any of these 3-Domain Cry Toxins may be selected to apply the method of this invention to obtain the respective DNA construction of the Modified 3-Domain Cry Toxins. The expression of these DNA constructions may be easily achieved, as shown in Example 2.

Preferably, the plasmid vector will be a vector with a double origin replication that may be replicated in the cells of *Escherichia coli* and *Bacillus thuringiensis*. The expression vectors may contain a selection marker, which is a protein coding gene necessary for the survival or for the growth of the host cell transformed with the vector. Typically, the selection marker genes encode for proteins that confer resistance to antibiotics or other substances (for example, ampicillin, neomycin, or methotrexate). The selection maker genes may also be genes that complement auxotrophic deficiencies or that provide critical nutrients not available in the complex medium. Choosing the proper selection marker gene will depend on the host cell; in the state of the art proper selection markers are known for different hosts.

The binding mix may be transformed into *E. coli* cells, and the transforming plasmid may then be purified and transformed into *B. thuringiensis* cells for the expression of Modified 3-Domain Cry Toxins and the production of bio-insecticides. Alternately, the Modified 3-Domain Cry Toxin gene may be expressed in heterological systems as other microorganisms using proper vectors (including bacteria, virus, algae, and yeasts) or other organisms including transgenic insect and plant cells. For transgenic plants, the vector must be proper for transformation and expression in plants (such as corn, cotton, and soy, or others), so that the engineered plants produce the Modified 3-Domain Cry Toxins. Plants transformed in this manner may be protected from the attack of the target insects that are resistant to the Unmodified 3-Domain Cry Toxins. The preferred uses for application in spray bioinsecticides of the Modified 3-Domain Cry Toxins include, without limitation, protection of vegetables and forests. The preferred infestations we are seeking to control in this way, include but are not limited to lepidopterous insects.

To demonstrate how this method works, proteic fragments were obtained from the Cry1Ab and Cry1Ac toxins which lack the α-1 helix, through the method of this invention as illustrated in Example 1.

The DNA constructions coding for Modified 3-domain Cry toxins that lack the α-1 helix obtained by the above described method are also included within the scope of this invention.

In Example 2, vectors containing the above mentioned constructions that encode the Modified 3-domain Cry toxins lacking the α-1 helix are illustrated, which are included within the scope of this invention. It is well known by experts in the technique that the selection of vectors will depend in particular on the host cells that are used. Genetically engineered host cells that contain the aforementioned vectors are also included, some preferred host cells include bacteria, in particular Gram-positive bacteria such as those of the *Bacillus* genus, or Gram-negative bacteria, such as *Pseudomonas* and *Escherichia*, and plant cells such as corn, soy, potato, cotton, and other plants.

The recombinant methods to produce Modified 3-Domain Cry Toxins of this invention shall be included within the scope of this invention. In general, these methods include the steps to cultivate genetically engineered host cells containing a vector that harbors DNA constructions of Modified 3-Domain Cry Toxins. Under proper growing conditions, genetically engineered host cells produce the Modified 3-Domain Cry Toxins. These methods also include the option to recover the Modified 3-Domain Cry Toxins from the cellular culture, either with spores, or as purified proteins, or contained within the host organism.

These methods are illustrated in Example 2 for the Modified 3-Domain Cry Toxins (Cry1AbMod and Cry1AcMod).

In another scope, coded modified 3-domain Cry toxins are described. Modified 3-Domain Cry Toxins do not require binding to the primary receptor to form the pre-pore oligomeric structure. Thus, given that the Modified 3-Domain Cry Toxins which lack the α-1 helix are toxic to the Eligible Resistant Insects, they both continue to be toxic for insects sensitive to the Unmodified 3-Domain Cry Toxins.

As mentioned above, after solubilization in the gut medium, the following three steps in the mode of action are: 1) Initial enzymatic cut by the proteases of the gut medium, causing removal of the N-terminal peptide from the C-terminal area (if it is present in the toxin); 2) binding to the primary receptor, and 3) second enzymatic cut causing removal of the α-1 helix. These three steps produce a protein capable of forming the oligomeric structure called pre-pore (FIG. 1).

A defective primary receptor (CADR) is the most important and common mechanism by which insects become resistant to the Cry toxins (Ganan et al, 2001, Ferre and Van Rie, 2002; Morin et al, 2003; Xu et al, 2005). Alterations in the primary receptor reduce or eliminate binding of the Unmodified 3-Domain Cry Toxins, apparently preventing the enzymatic cut of the α-1 helix and inhibiting the formation of the pre-pore oligomeric structure necessary for toxicity. Modified 3-Domain Cry Toxins lack the α-1 helix. In this way, in order to kill insects, these toxins do not require binding to the primary receptor, nor is required the cut associated with this binding that results in the loss of the α-1 helix. As they do not require binding to the primary receptor, the defects in the primary receptor that block the binding, do not block its toxicity. In other words, the Modified 3-Domain Cry Toxins suppress the resistance of insects because the interaction with the primary receptor is not required.

To illustrate these Modified 3-Domain Cry Toxins, DNA constructions were obtained that encode Modified Cry1Ab and Cry1Ac Toxins (lacking the α-1 helix) as shown in Example 1, and the Modified toxins were expressed as shown in Example 2.

To demonstrate that the Modified 3-Domain Cry Toxins are able to form pre-pore oligomeric structures, protoxins of the two Modified 3-Domain Cry Toxins, Cry1AbMod and Cry1AcMod, were treated only with the trypsin protease producing thus the 250 kDa oligomer. In contrast, the same treatment with trypsin of the protoxins of the two corresponding Unmodified 3-Domain Cry Toxins, Cry1Ab and Cry1Ac, only produced the 60 kDa monomer structure, as shown in Example 3.

The toxicity of the Modified 3-Domain Cry Toxins was determined by feeding resistant and vulnerable larvae in bioassays diets containing different concentrations of the Modified 3-Domain Cry Toxin. The toxicity of Cry1AbMod and Cry1AcMod was compared with that of their unmodified counterparts, Cry1Ab and Cry1Ac against the first stage vulnerable (wild) larvae of the pink bollworm (*Pectinophora gossypiella*) and pink bollworms that are resistance to Cry1Ab and Cry1Ac. The toxicity of Cry1AcMod was also compared with its counterpart, unmodified Cry1Ac, against first instar larvae of the vulnerable strains resistant to Cry1Ac of the diamondback worm. The Unmodified Cry1Ab and Cry1Ac toxins were highly toxic to vulnerable larvae, but not so for resistant larvae (Tables 1 and 2). In contrast, the Modified 3-Domain Cry Toxins, Cry1AbMod and Cry1AcMod killed the vulnerable larvae as well as the resistant ones (Tables 1 and 2). These results show that the Modified 3-Domain Cry Toxins used for example (Cry1AbMod and Cry1AcMod) suppressed the high level of resistance to the Unmodified Cry1A toxins in the Eligible Resistant Insects, that are associated with mutations that affect the expression of the primary receptor (CADR in the case of Cry1A), whether they are direct mutations in the gene of said primary receptor (as in the case of the pink bollworm) or in genes that indirectly affect the expression of the primary receptor (as in the case of the diamondback worm).

To test the toxicity of Modified 3-Domain Cry Toxins of this invention against another target insect, the *Manduca sexta*, for which populations of resistant insects have not yet been isolated or cultivated, *M. sexta* larvae were obtained with the CADR receptor silenced and they were tested to determine their resistance to the Unmodified Cry1Ab, as described in Example 5. With these *M. sexta* larvae (with the CADR receptor silenced) the toxicity of the Modified 3-Domain Cry Toxin, Cry1AbMod was tested, as described in Example 6. The results demonstrated once more that the Modified 3-Domain Cry Toxins kill insects that are resistant to the corresponding Unmodified 3-Domain Cry Toxins.

In another scope, this invention refers to the method to suppress the resistance of the Eligible Resistant Insects, which is based on killing said insects by allowing them to eat foods containing a sufficient amount of the Modified 3-Domain Cry Toxin of this invention. The lethal dose depends on many factors, including: the mixture of the excipient used; the technique and conditions of application; if the formulation is an aerosol, a film, or small particles; the thickness of the film or the size of the particles and others of this type. The resolution of these factors and other considerations suitable for determining the lethal dose of Modified 3-Domain Cry Toxins is within the abilities of professionals in the technical field.

To feed the Eligible Resistant Insects with Modified 3-Domain Cry Toxins, said toxins must be available within the diet of the insect populations. This may be done by applying formulations containing the Modified 3-domain Cry Toxins. This may also be done by generating transgenic plants that contain the DNA constructions that encode the Modified 3-Domain Cry Toxins linked in an operable manner to vectors of expression suitable for plants, in such a way that said transgenic plant produces the Modified 3-Domain Cry Toxins.

The formulations and the transgenic organisms may be used for agricultural crops, forests, and to control disease vectors. For example, some genetically altered trees exist that produce Bt toxins, also algae has been genetically altered to produce Bt toxins to control mosquitos.

To kill the Eligible Resistant Insects, formulations containing the Modified 3-Domain Cry Toxins may be applied periodically where the insect infestation feeds. For example, it may be applied to plants (leaves, stems, roots or other plant parts) to kill the Eligible Resistant Insects infesting crops or forests, and in bodies of water to kill the Eligible Resistant Insects that are human disease vectors living in the water during their larval stage (for Example, mosquitoes and black flies). This may done cyclically alternating applications of formulations containing Unmodified 3-Domain Cry Toxins (without the Modified 3-Domain Cry Toxins) with applications of formulations containing Modified 3-Domain Cry Toxins. The Unmodified 3-Domain Cry Toxins may be applied until the appearance of the Eligible Resistant Insects is calculated to take place or is observed, at which time the formulations containing the Modified 3-Domain Cry Toxins may be then applied to kill the resistant insects.

Another scope of this invention relates to new formulations or compounds that contain one or more Modified 3-Domain Cry Toxins to suppress the resistance of the Eligible Resistant Insects. In the formulations, the Modified 3-Domain Cry Toxins may be contained in host organisms or associated with spores or in a homogeneous preparation of pure proteins or in a mixture of spores with cultivated transformed organisms. The Modified 3-Domain Cry Toxins may also be contained in a non-sporing microorganism such as *Escherichia coli* or a sporing microorganism such as *Bacillus megaterium* or *B. thuringiensis*, associated with spores of the strain used to express them or as isolated crystals (and optionally a pure Cry protein) together with a mixture of excipients. The amount of the excipient mixture used will depend upon the potency desired in the formulation. In choosing the excipient mixture which are components in the formulation, the final purpose sought for the formulation should be considered. For Example, agronomically acceptable excipient mixtures must be used for formulations that will be applied to crops and ecologically acceptable excipients must be selected for formulations to be applied in forests (to control forest infestations of the Eligible Resistant Insects) and for bodies of water (to control the vector insects of the Eligible Resistant Insects).

The mixture of the excipients may include carriers, surfactant agents, UV protectors, and other components, and may take the form of wettable powders, liquid concentrates, granules, or other formulations. These formulations and procedures of application are well known in the technology.

The term "excipient" as it is used here, means an inert solid or liquid material, which may be inorganic or organic and of a synthetic or natural origin, with which the active compound is mixed or formulated to facilitate its application on plants, seeds, grounds, water, or other objects to be treated, or its storage, transport, and/or management. Any of the commonly used materials in the formulation of biopesticides—for example, acceptable additives in horticulture, agriculture, and ecology are suitable—.

Some suitable solid excipients are natural and synthetic clays and silicates, for example, natural silica such as diatomaceous earth; magnesium silicates, for example, talc; aluminum-magnesium silicates, for example, attapulgites and vermiculites; aluminum silicates, for example, kaolinites, montmorillonites, and micas; calcium carbonate; calcium sulfate; synthetic hydroxysilicone and synthetic calcium silicates; elements such as, for Example, carbon and sulfur; natural and synthetic resins such as, for example, coumarone resins, polyvinyl chloride and polymer and copolymer styrenes; bitumen; waxes such as, for example, bee's wax, paraffin wax, and chlorinated mineral waxes; solid fertilizers, for Example, superphosphates; and ground natural fibrous materials, such as ground corn cobs.

Examples of suitable liquid excipients are water, alcohols such as isopropyl and glycol alcohols; ketones such as acetone, methylethylketone, methylisobutylketone and cyclohexanone; ethers such as cellosolves; aromatic hydrocarbons such as benzene, toluene, and xylene; petroleum fractions such as kerosene, light mineral oils; chlorinated hydrocarbons such as carbon tetrachloride, perchloroethylene, and trichloromethane. Other suitable compounds are liquefied compounds, that are normally vapors or gases. Mixtures of different liquids are commonly suitable.

A surfactant agent may be added, which may be an emulsifying agent, a dispersing agent, or a moisturizing agent: may be non-ionic or ionic. Any of these surfactant agents usually applied in the formulation of herbicides or insecticides may be used. Some examples of suitable surfactant agents are the sodium and calcium salts of polyacrylic and sulfonic acids; products of fatty acid or aliphatic amine or amide condensation that contain at least 12 carbon atoms in the ethylene oxide and/or propylene oxide molecule; glycerol esters and fatty acid, sorbitan, saccharose, or pentanethiol; condensations of these with ethylene oxide and/or propylene oxide; products of fatty acid condensations or alkylphenols, for example, ρ-octylphenol or ρ-octylcresol, with ethylene oxide and/or propylene oxide; sulfates or sulfonates of these products of condensation, alkaline salts or alkaline earth metals, preferably sodium salts of sulfuric or sulfonic acid esters that contain at least 10 carbon atoms in the molecule, for example, sodium lauryl sulfate, secondary alkyl sodium sulfates, sodium salt of sulfonated castor oil, and sodium alkylaryl sulfonates such as sodium dodecylbenzene sulfonate; and ethylene oxide polymers and ethylene or propylene oxide copolymers.

Some examples of UV protectors are referenced in U.S. Pat. No. 5,141,744, where stable macrogels are described (for at least six months) that contain UV protectors (like octyl dimethyl PABA) that are used in pesticides including Bt toxins which offer advantages for protection against inactivation by sunlight. U.S. Pat. No. 4,094,969 discloses another manner to establish pesticide formulations that contain Bt toxins which rapidly degrade upon exposition to sunlight through the addition of sulfonated copolymers.

The compounds of this invention may be prepared as wettable powders, granules, solutions, emulsifiable concentrates, concentrates in suspension, and aerosols. The wettable powders are usually compounded to contain between 25 to 75% by weight of the active compound and usually contain, in addition to the solid carrier, between 3 and 10% by weight of a dispersing agent, 12 to 15% of a surfactant agent and, when necessary, up to 1 to 10% by weight of stabilizers and other additives such as penetrators or adhesives. The powders are usually formulated as a concentrate powder that has a composition that is similar to that of the wettable powders but without the dispersing or surfactant agents, and are diluted in the field with additional solid carriers in order to obtain a compound that usually contains between 0.5 and 10% by weight of the active compound. The granules are usually prepared to be of a size between 10 and 100 BS mesh (1,676-0.152 mm), and may be manufactured by agglomeration or impregnation techniques. Generally, the granules contain between 0.5 and 25% by weight of the active compound, 0 and 1% by weight of additives such as stabilizers, modifiers for slow release and agglutinating agents. Emulsifying concentrates usually contain, in addition to the solvent and, when necessary, the cosolvent between 10 and 20% by volume weight of the active compound, between 2 and 20% by volume weight of emulsifiers and between 0 and 20% by volume weight of appropriate additives such as stabilizers, penetrants, and corrosion inhibitors. Concentrates in suspension are compounded to obtain a stable, nonsettleable, and fluid product and usually contains between 0 and 75% by weight of the active compound, between 0.5 and 5% by weight of dispersing agents, between 1 and 5% of surfactant agents, between 0.1 and 10% by weight of suspension agents, such as antifoaming agents, corrosion inhibitors, stabilizers, especially for the protein, penetrants, and adhesives, and as a carrier, water or an organic liquid in which the active compound is substantially insoluble; certain organic solids or inorganic salts may be dissolved in the carrier to help prevent sedimentation or as antifreeze agents for water.

The water-dispersible granule formulations is in the form of hard, dry granules that are essentially free of powder and that are resistant to wear and handling, minimizing in this way the formation of powder. Upon contact with water, the granules disintegrate rapidly to form suspensions of particles of the active material. This type of formulations contains 90% or more by weight of the active material, between 3 and 7% by weight of ground surfactants, which act as dispersing humectants, suspension and agglutinating agents and between 1 and 3% by weight of a carrier, which acts as a suspension agent.

Aqueous dispersions and emulsions, for example, formulations obtained by diluting a wettable powder or concentrate in accordance with the invention with water, which also fall within the scope of this invention. Said emulsions may be of the water in oil type or of oil in water, or it may have a thick consistency like mayonnaise.

It is obvious from the aforementioned that this invention provides for formulations that contain as little as 0.0001% by weight and up to as much as 95% by weight of a Modified 3-Domain Cry Toxin of this invention as the active agent. Since commercial products are preferably formulated as concentrates, the final user normally uses dilute formulations of a substantially lower concentration.

The compounds of this invention also contain other active ingredients, for example, other compounds that possess pesticidal properties, especially insecticidal (particularly other Cry and Crt toxins), acaricidal, or fungicidal properties, as is suitable for the intended purpose.

Formulations containing the Modified 3-Domain Cry Toxins are prepared according to known methods, for example by homogeneous mixing and/or grinding the active ingredients with the carrier mix.

The Modified 3-Domain Cry Toxins of this invention also may be administered to the target insect infestation through transgenic plants that express these Modified Toxins. There are several commercially available transgenic Bt crops, including corn and cotton. The methods for constructing these and other transgenic plants to express the genes of Cry Bt toxins are well know by experts in the technology. Briefly, there are several methods to transform vegetable cells and tissues: The "Gene Pistol" method, also known as microprojectile or biolistic bombardment (see U.S. Pat. No. 4,945,050 issued to Cornell and U.S. Pat. No. 5,141,131 issued to DowElanco, now Dow AgroSciences, LLC); the electroporation method (see WO87/06614 issued to Boyce Thompson Institute and WO92/09696 and WO93/21335, both issued to Plant Genetic Systems) especially useful in the transformation of the monocotyledon species such as corn and rice; and the method mediated by Agrobacteriun (Vaeck et al 1987) that has been successfully practiced on dicotyledons (plants with large leaves such as soy and tomatoes) for many years, and has recently been effective in some monocotyledons (grass and other related plants) (see: U.S. Pat. No. 5,177,010 issued to the University of Toledo; U.S. Pat. No. 5,104,310 issued to Texas A&M; European Patent Applications 0131624131, 120516, 159418B1 and 176,112 issued to Schilperoot; U.S. Pat. Nos. 5,149,645, 5,469,976, 5,464,763, 4,940,838 and 4,693,976 issued to Schilperoot; European Patent Applications Nos. 116718, 290799, 320500 issued to the Max Planck Institute; European Patent Applications 0267159 and 0292435 and U.S. Pat. No. 5,231,019 issued to Ciba Geigy, now Novartis).

In general, the *Agrobacterium* method is considered preferable to the gene pistol, due to the high frequency of external DNA single-site insertion, making it easier to monitor. If *Agrobacterium* is used to transform plants, the DNA to be inserted in the genome of the plant must be cloned in special plasmids, either in an intermediate vector or in a binary vector. This method of transformation may be easily used by experts in the technology to transform plant with the constructions that contain the Modified 3-Domain Cry Toxins genes of this invention, to generate transgenic plants that kill or avoid the appearance of Eligible Resistant Insects in the field.

The following examples illustrate how the invention was conceived and put into practice and shows how it may be utilized. These examples must not be used to limit it. The description provided in the following examples relates to preferred methods of molecular biology using available strategies of published protocols for vector and other DNA molecule construction. All necessary molecular cloning and recombinant DNA techniques may be performed by standard methods (Sambrook et al., 1995).

EXAMPLES

Example 1

Use of this Invention's Method for Obtaining Examples of DNA Constructions that Encode Modified 3-Domain Cry Toxins Which Lack the α-1 Helix To illustrate this invention's method, two 3-Domain Cry Toxins were selected: Cry1Ab and Cry1Ac. The promoter area, the coding area of the complete protein and the α-1 helix were identified in both of these, as follows:

| Toxin Gene | Promoter Area | Coding Area of Complete Protein | N-Terminal and Coding Area of the α-1 Helix | Coding Area of the Toxin (from the α-2 helix to β-23) |
| --- | --- | --- | --- | --- |
| cry1Ab | 1-390 pb | 390-4272 pb | 390-538 pb | 538-2225 pb |
| cry1Ac | 11-401 pb | 401-4251 pb | 401-549 pb | 549-2236 pb | pb, pairs of bases

To exclude the coding area of the α-1 helix, genetic constructions were amplified for the Modified 3-domain Cry toxins called Cry1AbMod and Cry1AcMod, as follows:

In these cases, 3 PCR steps were performed as shown in FIG. 4. As a template, the total DNA of *Bacillus thuringiensis* strain Bt407 was used that contains the pHT315 Cry1Ab plasmid and the BtHD73 strain (which contain the Cry1Ab and Cry1Ac genes, respectively; according to that reported in the Gene Bank, access numbers X98793 and ML 1068, respectively). For the PCR1, the direct oligonucleotide, included the restriction site Hind III at the 5' end (which will be used for the insertion in a suitable vector) followed by the first 18 pb of the promoter area and the reverse oligonucleotide contains the ATG codon and the Neo I restriction site in the 5' end (to be linked with the PCR2 fragment).

The oligonucleotides for the PCR2 were designed to include a Neo I restriction site at 5' end of the direct oligonucleotide followed by the first 20 pb of the α-2 helix. The reverse oligonucleotide included the last 20 pb of the α-23 helix followed by the BamHI restriction site. (to be linked with the PCR3 fragment).

The direct oligonucleotide for the PCR3 were designed to include a BamHI restriction site at 5' end followed by the first 19 pb of the C-Terminal end of the protein. The reverse oligonucleotide included the last 21 pb of the terminator area and the SmaI restriction site at the 5' end (to be used for cloning in a suitable vector).

The three PCR fragments were purified and separately linked in the pBCKS vector, previously digested with the restriction enzymes corresponding to each PCR product. Finally, each pBCKS plasmid was purified and cut with the corresponding restriction enzymes to release the PCR fragments (PCR1 HindIII-Ncol; PCR2 Ncol-BamHI y PCR3

BamHI-SmaI). These PCR fragments were purified and linked in the double replication origin vector pHT-315 (Lereclus et al., 1989), previously digested with the restriction enzymes HindIII y SmaI. The resulting plasmids contained the modified versions of the cry1Ab y cry1Ac genes, which lack the coding area of the α-1 helix. These genes were called Cry1AbMod y Cry1AcMod.

Example 2

Obtaining Vectors and Host Cells that Contain DNA Constructions that Encode Modified 3-Domain Cry Toxins and Their Use in Recombinant Methods to Produce Modified 3-Domain Cry Toxins Vectors that included the genetic constructions Cry1AbMod y Cry1AcMod were obtained, cloning the genetic constructions in the double replication origin vector pHT-315 (Lereclus et al., 1989). The genetically altered host cells that contain the constructions were obtained by transforming the acrystallized strain Bt407 Cry (serotype HI, Lereclus et al., 1989), with the aforementioned vectors.

In order produce the Modified and Unmodified (wild) 3-Domain Cry Toxins of this Example, the transforming and wild strains were cultivated for 3 days in a shaking incubator at 29° C. and 200 rpm in a nutritious sporulation medium (Lereclus et al., 1995) supplemented with 10 μg of erythromycin per ml. The Modified and Unmodified 3-Domain Cry Toxin crystals were recovered and purified by saccharose gradient (Thomas and Ellar, 1983) and solubilized in 10 mM of buffer carbonates with a pH of 10.5. The protein samples were separated in 10% SDS-PAGE acrylamide gels (Laemmli, 1970). The genetically altered cells as well as those that were not altered produced proteins with an apparent molecular weight of approximately 130 kDa (FIG. 5).

Example 3

Formation of Modified 3-Domain Cry Toxin Oligomers Used as Example (Cry1AbMod and Cry1AcMod)

The in vitro formation of oligomers is facilitated by activating the Cry1A protoxins with proteases in the presence of Bt-R$_1$ protein fragments that contain binding areas to the toxin or in the presence of an scFv73 antibody that mimetizes these toxin binding areas to the CADR receptor (Gomez et al., 2003). The Cry1Ab protoxin produces a 250 kDa oligomer when it is incubated with CADR fragments that contain the 7-12, 11-12 or 12 repetitions of the CADR (FIG. 6).

When the Cry1AbMod and Cry1AcMod protoxins are treated with the protease trypsin in the absence of the CADR receptor, they produce a 250 kDa oligomer, while under these conditions the wild protoxins Cry1Ab and Cry1Ac do not form it, but only produce a 60 kDa monomer, (FIG. 7). These results indicate that the Modified 3-Domain Cry Toxins produce the 250 kDa oligomeric pre-pore when they are proteolytically activated in the absence of the primary receptor.

Example 4

The Toxicity of the Proteins Cry1Ab, Cry1Ac, Cry1AbMod and Cry1AcMod in Vulnerable and Resistant Strains of *Pectinophora gossypiella* (Pink Bollworm) and of *Plutella xylostella* (Diamondback Worm)

The most common type of resistance to Bt toxins, called "Mode 1" is linked to mutations on the CADR gene in several lepidopterous insects (Gahan et al, 2001; Morin et al, 2003; Xu et al, 2005). Nevertheless, in the case of the diamondback worm, type 1 resistance that presents in this insect is not linked to mutations in the cadherin gene (Baxter et al 2005).

The AZP-R resistant strain of the pink bollworm was obtained by selecting survivors of exposure to the Cry1Ac toxin in 10 cotton fields (Tabashnik et al., 2000). The repeated selection increased the resistance of the AZP-R strain to the Cry1Ac up to 3,100 times with respect to the vulnerable APHIS-S strain of the same worm (Tabashnik et al., 2002a). In the AZP-R strain of the pink bollworm, the resistance to the Cry1Ac is inherited recessively and is linked to 3 mutant alleles (r1, r2 and r3) of the CADR (BtR) gene (Morin et al, 2003). Individuals with any combination of 2 mutant r alleles are resistant to the toxin Cry1Ac and to transgenic cotton plants that produce this toxin (Morin et al, 2003). The AZP-R strain also presents a cross resistance to the toxin Cry1Ab and a reduction in the binding of the Cry1Ab toxin to the apical microvilli of the larval gut cells (Tabashnik et al, 2002b, Gonzalez-Cabrera et al., 2003). The diamondback worm is the only insect pest that has developed resistance to the Cry1Ac toxin applied in a spray form in the field (Tabashnik 2004).

In this experiment, we performed bioassays that confirmed that the Unmodified 3-Domain Cry Toxins used, for example: Cry1Ac and Cry1Ac were highly toxic for vulnerable larvae but not for the resistant larvae of the insects analyzed, the pink bollworm and the diamondback worm (Tables 1 and 2). At a concentration of 100 μg of the toxin per ml of diet, the survival of the resistant pink bollworm was high with the unmodified Cry1Ab and Cry1Ac (94% and 100% respectively). In contrast, the Modified 3-Domain Cry Toxins used for example (Cry1AbMod and Cry1AcMod) killed the killed the vulnerable larvae as well as the resistant ones. At a concentration of 30 μg of the toxin per ml of diet, the survival of the resistant pink bollworm was 0% with both Modified 3-Domain Cry Toxins, Cry1AbMod and Cry1AcMod (Table 2). These results show that the Modified 3-Domain Cry Toxins of this invention suppressed the high level of resistance to the corresponding Unmodified 3-Domain Cry Toxins of this example using the Eligible Resistant Insects, i.e., the larvae of the pink bollworm with resistance associated with mutations in the primary receptor. Table 2 shows that like the pink bollworm, the Cry1AcMod protein kills the resistant rPxAc diamondback worm, unlike the Cry1Ac protein that is not toxic for the rPxAc strain of the DBM. This strain's range of resistance is 30,000 times higher to the Cry1Ac toxin since the LC50 dose for the Cry1Ac toxin is 0.3 ng/well for the vulnerable DBM strain 31 and >10,000 ng/well for the resistant strain. In the case of the Cry1AcMod toxin, the range of resistance was reduced 5 times, since the LC$_{50}$ dose for Cry1AcMod is 20 ng/well for the vulnerable strain and 100 ng/well for the resistant rPxAc strain of the DBM.

TABLE 1

Cry1AbMod and Cry1AcMod toxins kill the pink bollworm that is resistant to the Cry1Ab and Cry1Ac toxins.

| Toxins | Concentration (μg toxin per ml diet) | Survival (%)* Vulnerable (APHIS-S) | Resistant (AZP) |
|---|---|---|---|
| Unmodified Toxins | | | |
| Cry1Ab | 1 | 0 | 90 |
|  | 10 | 0 | 100 |
|  | 100 | ND** | 80 |
| Cry1Ac | 1 | 0 | 94 |
|  | 10 | 0 | 98 |
|  | 100 | ND | 80 |
| Modified Toxins | | | |
| Cry1AbMod | 1 | 17 | 46 |
|  | 10 | 1.8 | 6.5 |
|  | 30 | 0 | 0 |
| Cry1AcMod | 1 | 88 | 88 |
|  | 10 | 12 | 7.5 |
|  | 30 | ND | 0 |

*The survival values were adjusted with the mortality of the control insects on an untreated diet. Adjusted survival was calculated by dividing the survival on a treated diet by the survival on the untreated diet. Size of sample = 40 to 80 larvae per strain per treatment.
**ND = not determined It was observed that at a concentration of 100 μg of the toxin per ml of diet, the survival of the pink bollworm was high with the Cry1Ab and Cry1Ac toxins (94% and 100% respectively). Whereas, at a concentration of 30 μg of the toxin per ml of diet, the survival of the resistant pink bollworm was 0% with both Cry1AbMod and Cry1AcMod toxins. Therefore, the modified toxins, Cry1AbMod and Cry1AcMod suppress the resistance of the pink bollworm to the unmodified toxins, Cry1Ab and Cry1Ac. At 10 μg of toxin per ml of diet, the modified toxins as well as the unmodified toxins killed more than 87% of the vulnerable larvae of the pink bollworm.

TABLE 2

The Cry1AcMod protein kills the diamondback worm that is resistant to the Cry1Ac toxin.

| Toxins | Concentration (μg toxin per ml diet) | Survival (%)* Vulnerable (PxGen88) | Resistant (rPxAc) |
|---|---|---|---|
| Unmodified Cry Toxins | | | |
| Cry1Ac | 0.2 | 0 | 97 |
|  | 2 | 0 | 100 |
|  | 20 | 0 | 90.6 |
| Modified Cry Toxins | | | |
| Cry1AcMod | 0.2 | 65.6 | 90.6 |
|  | 2 | 0 | 53 |
|  | 20 | 0 | 0 |

*The survival values were adjusted with the mortality of the control insects on an untreated diet. Adjusted survival was calculated by dividing the survival on a treated diet by the survival on the untreated diet. Size of sample = 32 larvae per strain per treatment.

We observed that at 20 micrograms (μg) of toxin per ml of diet, the number of survivors of the resistant survivorship of the diamondback worm was very high when they were treated with the toxin Cry1Ac (90.6%). Whereas, at a concentration of 20 μg of the toxin per ml of diet, the survival of the resistant strain of the diamondback worm was 0% when treated with the Cry1AcMod toxin. Therefore, the modified toxin, Cry1AcMod suppresses the resistance of the diamondback worm to the unmodified toxin, Cry1A. At 20 μg of toxin per ml of diet, the modified and unmodified Cry1Ac toxins killed 100% of the vulnerable insects of the diamondback worm.

Example 5

Silencing the CADR Receptor on *Manduca sexta* Larvae Reduces Vulnerability to the Cry1Ab Toxin To determine if the results with the pink bollworm extends to other lepidopterous insects, *Manduca sexta* larvae were created with a reduced vulnerability to the Cry1Ab toxin, using RNA interference (RNAi) to block the production of the CADR receptor (Bt-$R_1$). With RNAi, the double chain RNA (dsRNA) of a particular gene interferes with the translation of said gene inhibiting thusly the production of codified protein by this gene (Sijen et al, 2001). To produce dsRNA from the coding gene Bt-$R_1$ of *M. sexta* a fragment of 442 pb of the gene (from residue 8 to 155) was amplified by rtPCR from cDNA produced from samples of RNAm obtained from 5° instar larvae using the following oligonucleotides as first in the reaction of rtPCR GCTCTA-GAGCTGCCTTCCTGCTGGTGTTTA and GGAATTC-CTCCACGCGCACATTG AACAT. The 442 pb fragment was digested with the restriction enzymes XbaI and EcoRI and cloned in the pLITMUS 28i (HiScribe™) previously digested with the same restriction enzymes, this vector has two T7 promoter that flank a multi-cloning site. This permits amplification of the cloned fragments and the in vitro transcription of both DNA chains of the insert, generating dsRNA. FIG. 8 shows the dsRNA obtained by in vitro transcription of the Bt-$R_1$ gene fragment amplified using the T7 polymerase.

To prove if the Bt-$R_1$ protein may be silenced, first instar *M. sexta* larvae were injected in the hemolymph with either 1 μg of dsRNA of Bt-$R_1$ in 100 nl of water or with only 100 nl of water (control). After 12 hours on an artificial diet without toxins, survival was 74% for the 35 larvae injected with the dsRNA of Bt-$R_1$ and 75% for the 35 control larvae. Of the larvae that survived for 12 hours on an untreated diet, 24 of each of the larva groups injected with dsRNA or the control, were transferred to a diet treated with 20 ng of the protoxin Cry1Ab per $cm^2$. After 3 days on the diet treated with toxins, all the control larvae died while all the larvae injected with the dsRNA of Bt-$R_1$ survived (Table 3). Through a Western Blotting immunodetection assay using a specific anti-Bt-$R_1$ antibody, it was demonstrated that the injection of the dsRNA significantly reduced or completely eliminated the Bt-$R_1$ protein in the intestinal medium of the larvae (FIG. 9). The results of the bioassay and the immunodetection of Bt-$R_1$ indicate that the RNAi reduced the production of the Bt-$R_1$ protein and the vulnerability to the toxin Cry1Ab in the larvae of *Manduca sexta*.

TABLE 3

*M. sexta* larvae injected with Bt-$R_1$ dsRNA are not vulnerable to the Cry1Ab toxin.

| Treatment | No. larvae exposed to 20 ng Cry1Ab/$cm^2$ | Survival (%)* |
|---|---|---|
| $H_2O$ | 24 | 0 |
| dsRNA Bt-$R_1$ | 24 | 100 |

M. sexta larvae were injected with 100 nl of water or with 1 μg of the Bt-R$_1$ dsRNA in 100 nl of water and exposed to an artificial diet containing 20 ng of the Cry1Ab toxin per cm$^2$.

Example 6

Toxicity of the Cry1Ab and Cry1AbMod Toxins to M. sexta Larvae That Have Silenced the Bt-R$_1$ Receptor To determine if the Cry1AbMod is toxic to the larvae with reduced vulnerability to the wild Cry1Ab Toxin caused by silencing with Bt-R$_1$ RNAi, first instar M. sexta larvae were injected with 1 μg of Bt-R$_1$ dsRNA as described in Example 5. The larvae injected were fed diets supplemented with either 20 ng of the wild Cry1Ab protoxin or with 5 ng of the Cry1AbMod protoxin per cm$^2$. The larvae silenced in the Bt-R$_1$ by RNAi were not vulnerable to the wild Cry1Ab toxin but they were vulnerable to the modified Cry1AbMod toxin (FIG. 10)

These results show that one of the Modified 3-Domain Cry Toxins used, for example, the Cry1AbMod, suppresses the effect of reduced vulnerability caused by blocking the Bt-R$_1$ expression by RNAi in M. sexta larvae.

REFERENCES

Aronson A. I. and Shai Y. (2001) Why Bacillus thuringiensis insecticidal toxins are so effective: unique features of their mode of action. FEMS Microbial. Lett. 195, 1-8.

Baxter, S. W., Zhao, J.-Z., Gahan, L. J., Shelton, A. M., Tabashnik, B. E., Heckel, D. G. 2005. Novel genetic basis of field-evolved resistance to Bt toxins in Plutella xylostella. Insect Mol. Biol. 14, 327-334.

Boonserm, P., Davis, P., Ellar, D. J., Li, J. 2005. Crystal structure of the Mosquito-larvicidal Toxin cry4Ba and Its Biological Implications. J. Mol. Biol. 348, 363-382.

Boonserm, P., Mo, M., Angsuthanasombat, Ch., Lescar, J. 2006 Structure of the functional form of the mosquito larvicidal Cry4Aa toxin from Bacillus thuringiensis at a 2.8-angstrom resolution. J. Bacteriol. 188, 3391-3401.

Bravo, A., Gomez, I., Conde, J., Munoz-Garay, C., Sanchez, J., Zhuang, M., Gill, S. s., Soberon, M. (2004) Oligomerization triggers differential binding of a pore-forming toxin to a different receptor leading to efficient interaction with membrane microdomains. Biochem. Biophys. Acta. 1667, 38-46.

Crickmore N. Zeigler D. R. Feitelson J. Schnepf E. Van Rie J. Lereclus D. Baum J. and Dean D. H. (1998). Revision of the nomenclature for the Bacillus thuringiensis pesticidal crystal proteins. Microbiol. Mol. Biol. Rev. 807-813.

Crickmore N. Zeigler D. R. Schnepf E. Van Rief J. Lereclus D. Baum J Bravo A. and Dean D. H. "Bacillus thuringiensis toxin nomenclature" (2002) http://www.biols.susx-.ac.uk/Home/Neil,)Crickmore/Bt/index.html Conner a. J. Glare T. R. and Nap J.-P. (2003) The release of genetically modified crops into the environment. Part II. Overview of ecological risk assessment. The Plant Journal 33, 19-46.

De Maagd R. A. Bravo A. and Crickmore N. (2001) How Bacillus thuringiensis has evolved specific toxins to colonize the insect world. Trends in Genet. 17, 193-199. Ferré J. and Van Rie J. (2002) Biochemistry and genetics of insect resistance to Bacillus thuringiensis. Ann. Rev. Entomol. 47, 501-533.

Gahan L. J. Gould F. and Heckel D. g. (2001) Identification of a gene associated with Bt resistance in Heliothis virescens. Science. 293, 857-860.

Galitsky N. Cody V. Wojtczak A. Debashis g. Luft J. R. Pangborn W. and English L. (2001) structure of insecticidal bacterial β-endotoxin Cry 3Bb1 of Bacillus thuringiensis. Acta. Cryst. D57, 1101-1109.

Gomez I. Oltean D. I. Sanchez J. gill S. s. Bravo A. and Soberon M. (2001) Mapping the epitope in Cadherin-like receptors involved in Bacillus thuringiensis Cry1A toxin interaction using phage display. J. Biol. Chem. 276, 28906-28912.

Gomez I. Sanchez J. Miranda R. Bravo A. and Soberon M. (2002). Cadherin-like receptor binding facilitates proteolytic cleavage of helix α-1 in domain I and oligomer pre-pre formation of Bacillus thuringiensis Cry1Ab toxin. FEBS Lett. 513, 242-246.

Gomez I. Dean D. H. Bravo A. and Soberon M. (2003). Molecular basis for Bacillus thuringiensis Cry1Ab toxin speicficitry: Two structural determinants in the Manduca sexta Bt-R$_1$ receptor interact with loops α-8 and 2 in domain II of Cry1Abtoxin. Biochemistry. 42,10482-10489.

Gonzalez-Cabrera, J., B. Escriche, B. e. Tabashnik and J. Ferre. 2003. Binding of Bacillus thuringiensis toxins in resistant and susceptible strains of pink bollworm (Pectinophora gossypiella). Insect Biochem. Mol. Biol. 33:929-935.

Grochulski P. Masson L. Borisova s. Pustai-Carey M. Schwartz J. L. Brousseau R. and Cygler M. (1995) Bacillus thuringiensis Cry1A(a) insecticidal toxin: Crystal structure and channel formation J. Mol. Biol. 254, 447-464.

Gould, F. (1998) Sustainability of transgenic insecticidal cultivars: integrating pest genetics and ecology. Ann. Rev. Entomol. 43, 701-726.

Helgason E. Okstad O. a. Caugant D. A. Johansen H. A. Fouet a. Mock M. hegna I and Kolsto A. B. (2000). Bacillus anthracis, Bacillus cereus, and Bacillus thuringiensis-one species on the basis of genetic evidence. Appl. Environ. Microbiol., 66, 2627-2630.

Herrero, S., Gonzalez-Cabrera, J. Ferre. J., Bakker, P. L., de Maagd, R. a. 92004) Mutation sin the Bacillus thuringiensis Cry1Ca toxin demonstrate the role of domains II and III in specificity towards Spodoptera exigua larvae. Biochem. J. 384, 507-513.

James, c. 2005. Global status of biotech/GM Crops in 2005. 2005. ISAAA Briefs No. 34. Ithaca, N.Y., International Service for the Acquisition of Agri-biotech Applications.

Janmaat, A. F., and H. J. Myers. (2003) Rapid evolution and the cost of resistance to Bacillus thuringiensis in greenhouse populations of cabbage loopers, Trichoplusia ni. Proc. Roy. Soc. Lond. B. 270, 2263-2270.

Jurat-Fuentes, J. L., Adang, M. J. (2004) Characterization of a Cry1Ac-receptor alkaline phosphatase in susceptible and resistant Heliothis virescens larvae. Eur. J. Biochem. 271, 3127-3135.

Jura-fuentes, J. L., Adang, M. J. (2006) Cry toxin mode of action in susceptible and resistant Heliothis virescens larvae. J. Invertebr. Pathol. 92, 166-172.

Knight P. Crickmor eN. And Ellar d. J. (1994) the receptor for Bacillus thuringiensis Cry1A(c) delta-endotoxin in the brush border membrane of the lepidopteran Manduca sexta is aminopeptidase N. Mol. Microbiol. 11, 429-436.

Laemmli, U. K. (1970) Cleavage of structural proteins during the assembly of the head of bacteriophage T4, Nature 227, 680-685.

Lereclus D. Arantes O. Chaufaux J. and Lecadet M.-M. (1989) transformation and expression of a cloned delta-endotoxin gene in *Bacillus thuringiensis*. *FEMS Microbiol. Lett.* 60, 211-218.

Lereclus D., Agaisse H., Gominet M. Chafaux J. 1995. Overproduction of encapsulated insecticidal crystal proteins in a *Bacillus thuringiensis* spo0Amutant *Biotechnology* 13, 67-71.

Li J. Carroll J. and Ellar D. J. (1991) Crystal structure of insecticidal delta-endotoxins from *Bacillus thuringiensis* at 2.5 A resolution. *Nature* 353, 815-821.

Morin S. Biggs R. W. Shriver L. Ellers-Kirk C. Higginson D. Holley D. Gahan, Heckel D. G. Carriere Y. Dennehy T. J. Brown J. K. and Tabasnik b. E. 92003) Three cadherin alleles associated with resistance to *Bacillus thuringiensis* in pink bollworm. *Proc. Nat. Acad. Sci.* 100, 5004-5009.

Morse R. J. yamamoto t. and Stroud. R. M. (2001) Structure of Cry2Aa suggests an unexpected receptor binding epitope. *Structure* 9, 409-417.

Munoz-Garay, C., Sanchez, J. Darszon, A., de Maagd, R., Bakker, P, Soberon M., and Bravo, A. 92006) Permeability changes of *Manduca sexta* Midgut Brush Border Membranes Induced by Oligomeric Structures of Different Cry Toxins. *J. Membr. Boil.* In the press.

Pardo-Lopez, L., Gomez, I., Rausell, C., Sanchez, J., Soberon, M. and Bravo, A. 2006 Structural changes of th eCry1Ac oligomeric pre-pore from *Bacillus thuringiensis* induced by N-acetylgalactosmaine facilitates toxin membrane insertion. *Biochemistry* 45: 10329-10336.

Rausell, c., Munoz-Garay, C., Miranda-CassoLuengo, R., Gomez, I., Rudino-Pinera, E., Soberon, M. Bravo, A. (2004a). Tryptophan spectroscopy studies and black lipid bilayer analysis indicate that the oligomeric structure of Cry1Ab toxin from *Bacillus thuringiensis* is the membrane-insertion intermediate. *Biochem.* 43, 166-174.

Rausell C., Garcia-Robles, L., Sanchez J., Munoz-Garay c., Martinez-Ramirez, A. C., real, M.d., Bravo A. (2004b) Role of toxin activaqtion on binding and pore formation activity of the *Bacillus thuringiensis* Cry3 toxins in membranes of *Leptinotarsa decemlineata* [Say]. *Biochem. Biophyus Acta* 1660, 99-105.

Schnepf E. Crickmore N. Van Rie J. Lereclus D. Baum J. R/Feitelson J. Zeigler D. and Dean, D. H. (1998) *Bacillus thuringiensis* and its pesticidal crystal proteins. *MicrobioL Mol. Biol. Rev.,* 62, 705-806.

Schuler J. L. Lu Y. J. Sohnlein P. Brosseau R. Laprade R. Masson L. and Adang M. J. (1997) Ion channels formed in planar lipid bilayers by *Bacillus thuringiensis* toxins in the presence of *Manduca sexta* midgut receptors. *FEBs Lett.* 412, 270-276.

Sijen T. Fleenor J. Simmer f. Thijssen K. L. Parrish S. Timmons L. Plasterk R. H. and Fire A. (2001) On the role of RNA amplification in dsRNA-triggered gene silencing. *Cell.* 107, 465-476.

Tabashnik B. E. Finson N. Johnson M. W. Heckel D. G. (1994) Cross-Resistance to *Bacillus thuringiensis* Toxin Cry1F in the Diamondback Moth (*Plutella xylostella*). *Appl. Envirn Microbiol.* 60(12):4627-4629.

Tabashnik B. E. Patin A. L. Dennehy T. J. Lieu Y. B. Carriere Y. Sims M. A. and Antilla L. (2000) Frequency f resistance to *Bacillus thuringiensis* in field populations of pink bollworm. *Proc. Natl. Acad. Sci.* U.S.A. 97, 12980-12984.

Tabashnik, B. E., Y. G. Liu, T. J. Dennehy, M. A. Sims, M. S. Sisterson, R. W. Biggs and Y. Carriere, 2002a, Inheritance of resistance to Bt toxin Cry1Ac in a field-derived strain of pink bollworm (Lepidoptera: Gelechiidae). J. Econ. Entomol. 95:1018-1026.

Tabashnik, B. E., T. J. Dennehy, M. A. Sims, K. Larkin, G. P. Head, W. J. Moar and Y. Carriere. 2002b. Control of resistant pink bollworm by transgenic cotton with *Bacillus thuringiensis* toxin Cry2Ab. Appl. Environ. Microbiol. 68: 3790-3794.

Tabashnik, B. E., Carriere, Y., Dennehy, T. J. Morin, S., Sisterson, M. S. Roush, R. T., Shelton, A. M. and Zhao, J-Z (2003) Insect resistance to transgenic Bt Crops: Lessons from the Laboratory and field. *J. Econom. Entomol.* 96, 1031-1038.

Tabashnik, b. e., Dennehy, T. J., an dCarriere, Y. (2005) Delayed resistance to transgenic cotton in pink bollworm. *Proc. Nat. Acad. Sci.,* 102, 15389-15393.

Thomas, W. E., and Ellar, D. J. (1983) *Bacillus thuringiensis* var *israelensis crystal* delta-endotoxin: effect in insect and mammalian cells in vitro, *J. Cell Sci.* 60, 181-197.

Vadlamudi, R. K., Weber, E., Ji, I., Ji, t. H. and Bulla, L. A. Jr. (1995) Cloning and expression of a receptor for an insecticidal toxin of *Bacillus thuringiensis*. *J. Biol. Chem.* 270, 5490-5494.

Vaeck, M., Reynaerts, A., Hofte, H., Jansens, S., De Beuckekeer, M., Dean, C., Zabeau, M., van Montagu, M. and Leemans J. 1987 Transgenic plants protected from insect attack. Nature 328, 33-37.

Valaitis A. P. Jenkins J. L. Lee M. K. Dean D. H. and Garner K. J. (2001) Isolation an partial characterization of Gypsy moth BTR-270 an anionic brush border membrane glycoconjugate that binds *Bacillus thuringiensis* Cry1A toxins with high affinity. *Arch. Ins. Biochem. PhysioL* 46, 186-200.

Xu, X., Yu, L., and Wu, Y. (2005) Disruption of a cadherin gene associated with resistance of Cry1Ac delta-endotoxin of *Bacillus thuringiensis* in *Helicoverpa armigera*. *Appl. Environ. Microbiol.* 71, 948-954.

What is claimed is:

1. A method to suppress the resistance of an Eligible Resistant Insect, comprising the step of feeding said Eligible Resistant Insect a lethal dose of a Modified 3-Domain Cry Toxin selected from a Cry1Ab and Cry1Ac toxin, wherein the modification consists of the deletion of the amino acids forming α-1 helix of the native Cry1Ab and Cry1Ac Toxin.

2. The method of claim 1, wherein said Modified 3-Domain Cry Toxin is fed as part of a compound.

3. The method of claim 1, wherein said Modified 3-Domain Cry Toxin is expressed in a transgenic plant.

4. The method of claim 1, wherein the Eligible Resistant Insect is a Lepidopteran.

5. The method of claim 1, wherein the Eligible Resistant Insect is in the Genus *Heliothis, Pectinophora, Plutella, Manduca* or *Helicoverpa*.

6. The method of claim 1, wherein the Eligible Resistant Insect is selected from *Heliothis virescens, Pectinophora gossypiella, Plutella xylostella, Manduca sexta*, and *Helicoverpa armigera*.

* * * * *

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide Primer

<400> SEQUENCE: 1
```

```
gctctagagc tgccttcctg ctggtgttta                                    30
```

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide Primer

<400> SEQUENCE: 2

```
ggaattcctc cacgcgcaca ttgaacat                                      28
```